(12) United States Patent
Kai et al.

(10) Patent No.: US 8,008,657 B2
(45) Date of Patent: Aug. 30, 2011

(54) COMPOUND FOR ORGANIC ELECTROLUMINESCENT DEVICE AND ORGANIC ELECTROLUMINESCENT DEVICE

(75) Inventors: Takahiro Kai, Kitakyushu (JP); Masaki Komori, Kitakyushu (JP); Toshihiro Yamamoto, Kitakyushu (JP); Katsuhide Noguchi, Kitakyushu (JP); Hiroshi Miyazaki, Kitakyushu (JP)

(73) Assignee: Nippon Steel Chemical Co., Ltd., Tokyo (JP)

( * ) Notice: Subject to any disclaimer, the term of this patent is extended or adjusted under 35 U.S.C. 154(b) by 13 days.

(21) Appl. No.: 12/600,773

(22) PCT Filed: May 28, 2008

(86) PCT No.: PCT/JP2008/059807
§ 371 (c)(1),
(2), (4) Date: Nov. 18, 2009

(87) PCT Pub. No.: WO2008/146839
PCT Pub. Date: Dec. 4, 2008

(65) Prior Publication Data
US 2010/0148161 A1 Jun. 17, 2010

(30) Foreign Application Priority Data
May 29, 2007 (JP) ................................ 2007-142274

(51) Int. Cl.
*H01L 35/24* (2006.01)
(52) U.S. Cl. ..... 257/40; 257/84; 257/103; 257/E21.305; 257/E21.349; 257/E21.411; 257/E21.412

(58) Field of Classification Search .................... 257/40, 257/84, 103, E21.305, E21.349, E21.411, 257/E21.412
See application file for complete search history.

(56) References Cited

U.S. PATENT DOCUMENTS

2006/0124921 A1 6/2006 Ong et al.

FOREIGN PATENT DOCUMENTS

| EP | 1 956 022 A1 | 8/2008 |
|---|---|---|
| EP | 1 956 666 A1 | 8/2008 |
| EP | 2 080 762 A1 | 7/2009 |
| JP | 11-162650 | 6/1999 |
| JP | 11-176578 | 7/1999 |
| JP | 2001-313178 | 11/2001 |
| JP | 2002-305083 | 10/2002 |
| JP | 2002-352957 | 12/2002 |
| JP | 2003-142264 | 5/2003 |
| JP | 2003-515897 | 5/2003 |
| JP | 2006-193729 A | 7/2006 |
| WO | WO 01/41512 | 6/2001 |
| WO | WO-2007/063754 A1 | 6/2007 |
| WO | WO-2007/063796 A1 | 6/2007 |
| WO | WO-2008/056746 A1 | 5/2008 |

*Primary Examiner* — Long Pham
(74) *Attorney, Agent, or Firm* — Birch, Stewart, Kolasch & Birch, LLP

(57) ABSTRACT

Disclosed are an organic electroluminescent device (organic EL device) which is improved in luminous efficiency, fully secured of driving stability, and of simple constitution and a compound useful for the fabrication of said organic EL device. The compound for the organic EL device has an indolocarbazole structure or a structure similar thereto in the molecule wherein an aromatic group is bonded to the nitrogen atom in the indolocarbazole. The organic EL device has a light-emitting layer disposed between an anode and a cathode piled one upon another on a substrate and said light-emitting layer comprises a phosphorescent dopant and the aforementioned compound for an organic electroluminescent device as a host material.

6 Claims, 1 Drawing Sheet

US 8,008,657 B2

COMPOUND FOR ORGANIC ELECTROLUMINESCENT DEVICE AND ORGANIC ELECTROLUMINESCENT DEVICE

FIELD OF TECHNOLOGY

This invention relates to a novel compound for an organic electroluminescent device and to an organic electroluminescent device (hereinafter referred to as organic EL device) and, more particularly, to an organic EL device which emits light of high luminance by using simultaneously a phosphorescent dopant and a host compound of a specific structure.

BACKGROUND TECHNOLOGY

An organic electroluminescent device in the simplest structure is generally constituted of a light-emitting layer and a pair of counter electrodes sandwiching said light-emitting layer and functions by utilizing the following phenomenon. Upon application of an electrical field between the electrodes, electrons injected from the cathode and holes injected from the anode recombine in the light-emitting layer and the energy level after the recombination returns from the conduction band to the valence band with release of energy in the form of light.

In recent years, organic thin films have been used in the development of EL devices. In particular, in order to enhance the luminous efficiency, the kind of electrodes has been optimized for the purpose of improving the efficiency of injecting carriers from the electrodes and a device has been developed in which a hole-transporting layer of an aromatic diamine and a light-emitting layer of 8-hydroxyquinoline aluminum complex (hereinafter referred to as Alq3) are disposed in thin film between the electrodes. This device has brought about a marked improvement in the luminous efficiency over the conventional devices utilizing single crystals of anthracene and the like and thereafter the developmental works of organic EL devices have been focused on commercial applications to high-performance flat panels featuring self-luminescence and high-speed response.

In another effort to enhance the luminous efficiency of the device, the use of phosphorescence in place of fluorescence is investigated. The aforementioned device comprising a hole-transporting layer of an aromatic diamine and a light-emitting layer of Alq3 and many other devices utilize fluorescence. The use of phosphorescence, that is, emission of light from the excited triplet state is expected to enhance the luminous efficiency approximately three times that of the conventional devices utilizing fluorescence (emission of light from the excited singlet state). To achieve this objective, the use of coumarin derivatives and benzophenone derivatives in the light-emitting layer has been investigated, but these compounds merely produced luminance at an extremely low level. Thereafter, europium complexes were tried to utilize the excited triplet state, but they too failed to emit light at high efficiency. As is cited in the patent document 1, a large number of proposals have been made on the phosphorescent dopants.

Patent document 1: JP2003-515897 A
Patent document 2: JP2001-313178 A
Patent document 3: JP2002-305083 A
Patent document 4: JP2002-352957 A
Patent document 5: JPH11-162650 A
Patent document 6: JPH11-176578 A
Patent document 7: JP2003-142264 A What is proposed for a host material to be used in the light-emitting layer in the development of organic EL devices is CBP or a carbazole compound presented in the patent document 2. Since CBP is characterized by having a good hole transfer property but a poor electron transfer property, the use of CBP as a host material for tris(2-phenylpyridine) iridium (hereinafter referred to as Ir(ppy)3), a green phosphorescent emitter, disturbs balanced injection of electrical charges and causes excess holes to flow out to the side of the electron-transporting layer. As a result, the luminous efficiency from Ir(ppy)3 decreases.

One of the means to solve the aforementioned problems is to provide a hole-blocking layer between the light-emitting layer and the electron-transporting layer as described, for example, in the patent document 3. This hole-blocking layer accumulates holes efficiently in the light-emitting layer and contributes to improve the probability of recombination of holes and electrons in the light-emitting layer and enhance the luminous efficiency. Currently, the hole-blocking materials in general use include 2,9-dimethyl-4,7-diphenyl-1,10-phenanthroline (hereinafter referred to as BCP) and p-phenylphenolato-bis(2-methyl-8-quinolinolato-N1,O8)aluminum (hereinafter referred to as BAlq). These materials are able to prevent electrons and holes from recombining in the electron-transporting layer. However, BCP tends to crystallize even at room temperature and lacks reliability as a hole-blocking material and the life of the device is extremely short. BAlq is reported to have a Tg of approximately 100° C. and provide a relatively long life, but it has an insufficient hole-blocking ability and the luminous efficiency from Ir(ppy)3 decreases.

On the other hand, 3-phenyl-4-(1'-naphthyl)-5-phenyl-1,2,4-triazole (hereinafter referred to as TAZ) presented in the patent document 4 is also proposed for a host material of phosphorescent organic EL devices; however, since TAZ has a good electron transfer property but a poor hole transfer property, the light-emitting region is shifted to the side of the hole-transporting layer. Therefore, it is conceivable that some of the materials used for the hole-transporting layer have a problem in compatibility with Ir(ppy)3 and decrease the luminous efficiency from Ir(ppy)3. For example, 4,4'-bis[N-(1-naphthyl)-N-phenylamino]biphenyl (hereinafter referred to as NPB), which is used most widely in the hole-transporting layer from the viewpoint of high performance, high reliability, and long life, shows poor compatibility with Ir(ppy)3; hence, the problem with NPB is that the energy transfer occurs from Ir(ppy)3 to NPB and the luminous efficiency decreases.

Furthermore, the aforementioned BAlq that has an adequate electron transfer property is proposed for a host material of phosphorescent organic EL devices in the patent document 7. The document states that a phosphorescent organic EL device of long life can be realized without complicating the layered structure; however, it cannot be said that the use of BAlq in the proposed manner is sufficient for practical use.

Moreover, the patent documents 5 and 6 disclose some indolocarbazole compounds, but not the compounds of this invention. These documents recommend the use of the indolocarbazole compounds disclosed therein as a hole-transporting material, but contain no account to teach their use as a phosphorescent host material.

DISCLOSURE OF THE INVENTION

Problems to be Solved by the Invention

In applications of organic EL devices to display devices such as flat panel displays, it is necessary to improve the luminous efficiency of the device and, at the same time, to fully secure the driving stability of the device. Under the aforementioned circumstances, an object of this invention is to provide an organic EL device that performs at high efficiency with good driving stability and is practically useful and to provide a compound suitable therefor.

Means to Solve the Problems

The inventors of this invention have undertaken intensive studies, found that the aforementioned problems can be solved by using a compound of a specific indolocarbazole skeleton or a skeleton similar thereto for an organic EL device, and completed this invention.

A compound for an organic electroluminescent device according to this invention is represented by the following general formula W.

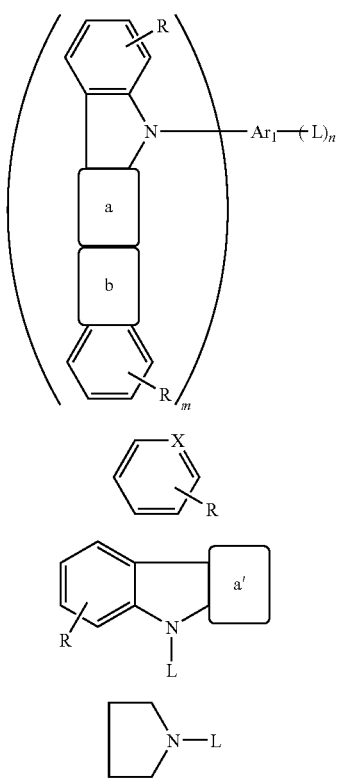

Wherein,
ring a is an aromatic or heterocyclic ring condensed with two adjacent rings and represented by formula (a1) or (a2), ring a' is an aromatic or heterocyclic ring condensed with three adjacent rings and represented by formula (a1), X is CH or N, and ring b is a heterocyclic ring condensed with two adjacent rings and represented by formula (b1);
$Ar_1$ is an aromatic heterocyclic group with a valence of m+n,
L is independently a substituted or unsubstituted aromatic hydrocarbon group or a substituted or unsubstituted aromatic heterocyclic group and at least one has a condensed ring structure;
R is independently hydrogen, alkyl group, aralkyl group, alkenyl group, alkynyl group, cyano group, dialkylamino group, diarylamino group, dialkylamino group, amino group, nitro group, acyl group, alkoxycarbonyl group, carboxyl group, alkoxyl group, alkylsulfonyl group, haloalkyl group, hydroxyl group, amide group, a substituted or unsubstituted aromatic hydrocarbon group, or a substituted or unsubstituted aromatic heterocyclic group; and
m is 1 and n is 1 or 2.

The compounds for an organic electroluminescent device represented by general formula (I) include the compounds represented by the following general formulas (II) to (IV).

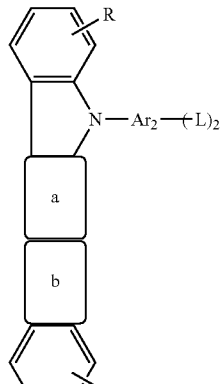

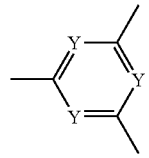

Wherein,
ring a, ring b, L, and R respectively have the same meaning as ring a, ring b, L, and R in general formula (I);
$Ar_2$ is a trivalent group represented by formula (c1) and Y is independently CH or N and at least one is N.

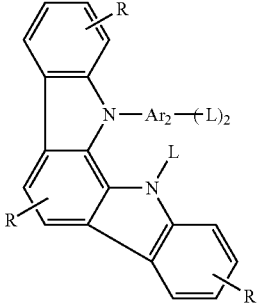

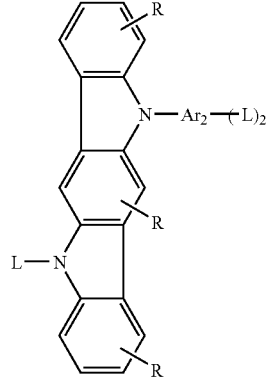

In general formulas (III) and (IV),
L, R, and Ar respectively have the same meaning as L, R, and Ar₂ in general formula (II).

Further, this invention relates to an organic electroluminescent device wherein a light-emitting layer is disposed between an anode and a cathode piled one upon another on a substrate and said light-emitting layer comprises a phosphorescent dopant and the aforementioned compound for an organic electroluminescent device as a host material.

The aforementioned organic electroluminescent device preferably has a hole-injecting/transporting layer disposed between the anode and the light-emitting layer and an electron-injecting/transporting layer disposed between the cathode and the light-emitting layer; moreover, it preferably has a hole-blocking layer disposed between the light-emitting layer and the electron-injecting/transporting layer.

The compounds represented by general formula (I) wherein m=2 include the compounds represented by the following general formula (V) and they are also useful as a compound for an organic electroluminescent device. Furthermore, the compounds represented by general formula (V) include the compounds represented by general formulas (VI) and (VII).

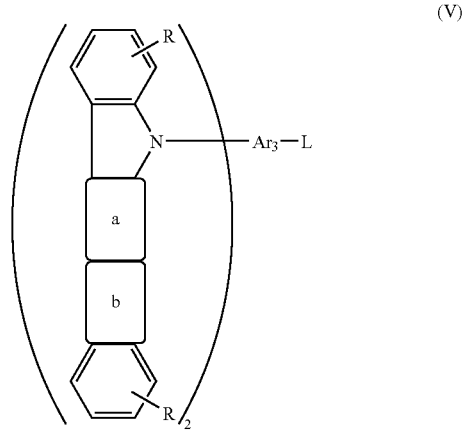

(V)

Wherein, ring a, ring b, L, and R respectively have the same meaning as ring a, ring b, L, and R in general formula (I), and Ar₃ is a trivalent aromatic heterocyclic group.

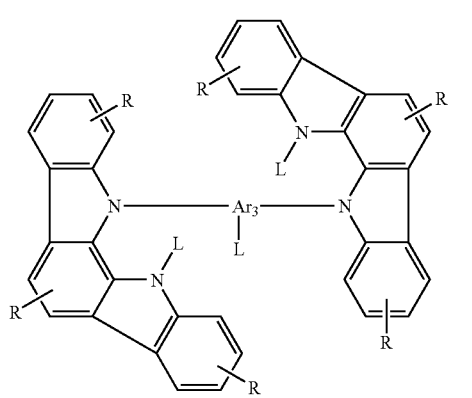

(VI)

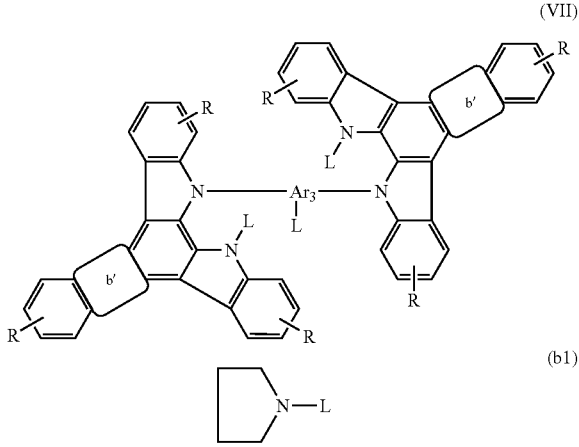

(VII)

(b1)

In general formulas (VI) and (VII),

L, R, and Ar₃ respectively have the same meaning as L, R, and Ar₃ in general formula (V), and ring b' is independently a heterocyclic ring condensed with two adjacent rings and represented by formula (b1).

A compound represented by any of general formulas (V) to (VII) wherein Ar₃ is a trivalent group represented by the aforementioned formula (c1) provides an excellent compound for an organic electroluminescent device.

A mode of reduction to practice of this invention will be described in detail below.

A compound for an organic electroluminescent device according to this invention is represented by any of the aforementioned general formulas (I) to (IV). Preferable examples of the compounds represented by general formula (I) include the compounds represented by general formula (II) and preferable examples of the compounds represented by general formula (II) include the compounds represented by general formulas (III) and (IV).

General formula (II) corresponds to general formula (I) wherein m is 1 and n is 2.

In general formulas (I) and (II), ring a is an aromatic or heterocyclic ring condensed with two adjacent rings and represented by formula (a1) or (a2), ring a' is an aromatic or heterocyclic ring condensed with three adjacent rings and represented by formula (a1), X is CH or N, and ring b is a heterocyclic ring condensed with two adjacent rings and represented by formula (b1). Preferable examples of these rings can be understood from general formulas (III) and (IV).

The group Ar is an aromatic heterocyclic group with a valence of m+n; Ar can have a valence of 2 to 4, but preferably it is a trivalent group and, more preferably, it is a trivalent group represented by formula (c1); m is 1 and n is 1 or 2, preferably 2; Ar₂ is preferably a trivalent group represented by formula (c1).

The group L is independently a substituted or unsubstituted aromatic hydrocarbon group or a substituted or unsubstituted aromatic heterocyclic group and at least one has a condensed ring structure. Such condensed rings include aromatic hydrocarbon rings or aromatic heterocyclic rings formed by condensation of 2 to 3 aromatic rings. In the case where the aromatic hydrocarbon groups or aromatic heterocyclic groups have substituents, preferable examples of the substituent include a group such as R to be described below.

The group R is independently a hydrogen, an alkyl group, an aralkyl group, an alkenyl group, an alkynyl group, a cyano group, a dialkylamino group, a diarylamino group, a diaralkylamino group, an amino group, a nitro group, an acyl group, an alkoxycarbonyl group, a carboxyl group, an alkoxyl group, an alkylsulfonyl group, a haloalkyl group, a hydroxyl group, an amide group, a substituted or unsubstituted aromatic hydrocarbon group, or a substituted or unsubstituted aromatic heterocyclic group. Preferred is a hydrogen. In the case where R is an alkyl group, an alkoxyl group, an alkylsulfonyl group, a haloalkyl group, or an alkoxycarbonyl group, the number of carbons in R is preferably 1 to 6. In the case where R is an alkenyl group or an alkynyl group, the number of carbons in R is preferably 2 to 6. In the case where R is an acyl group, a dialkylamino group, a diarylamino group, or a diaralkylamino group, the number of carbons in R is preferably 2 to 16.

The compounds represented by general formulas (I) to (IV) can be prepared readily by a known method. For example, they can be prepared by a sequence of reactions shown below with reference to a synthetic example described in Synlett, 2005, No. 1, pp. 42-48.

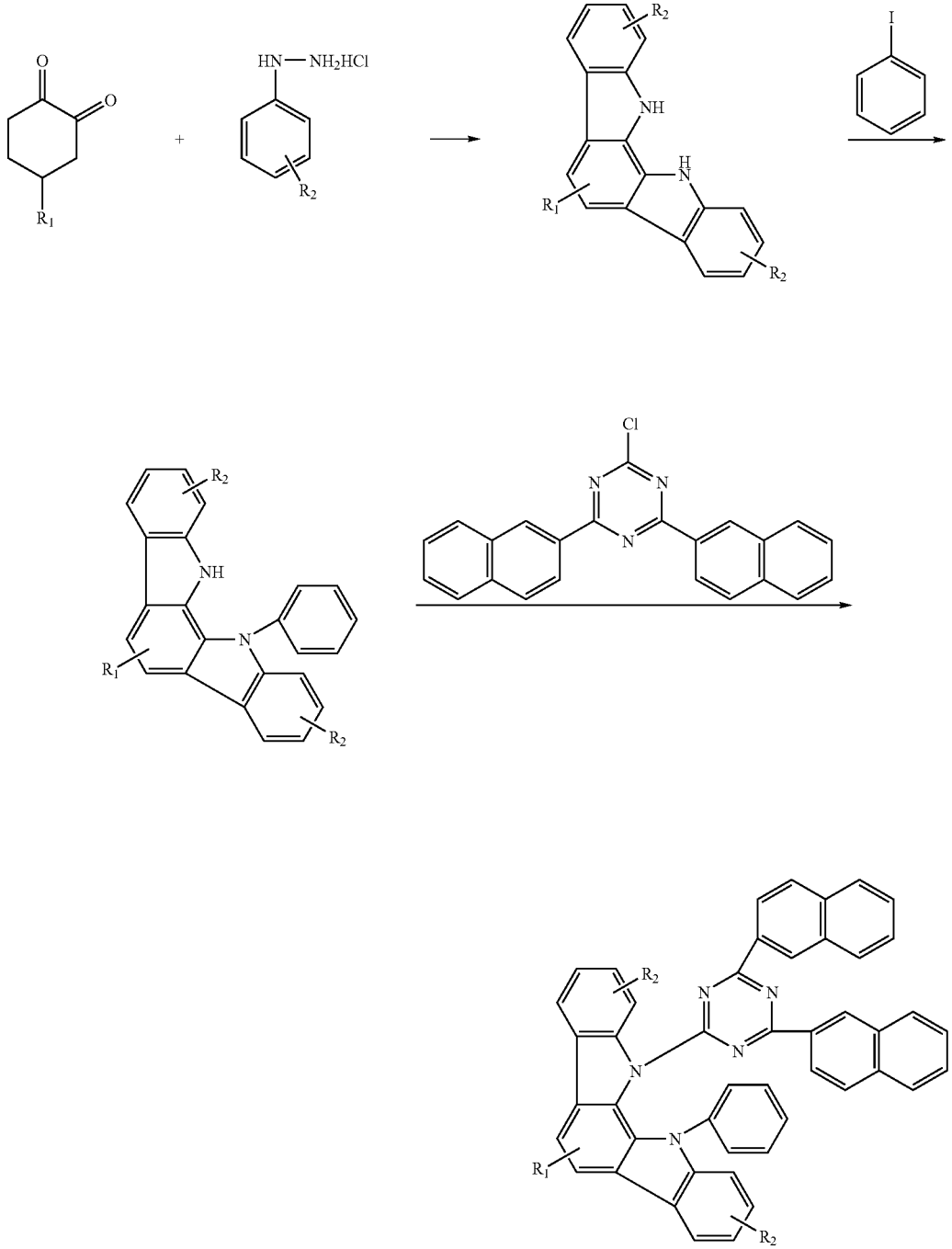

In general formulas (I) to (IV), $Ar_1$ and $Ar_2$ are aromatic heterocyclic groups, preferably trivalent groups. Preferable examples of $Ar_1$ and $Ar_2$ include Ar-1 to Ar-11 shown below. In these examples, two valences each is bonded to L and one valence is bonded to the ring nitrogen atom.

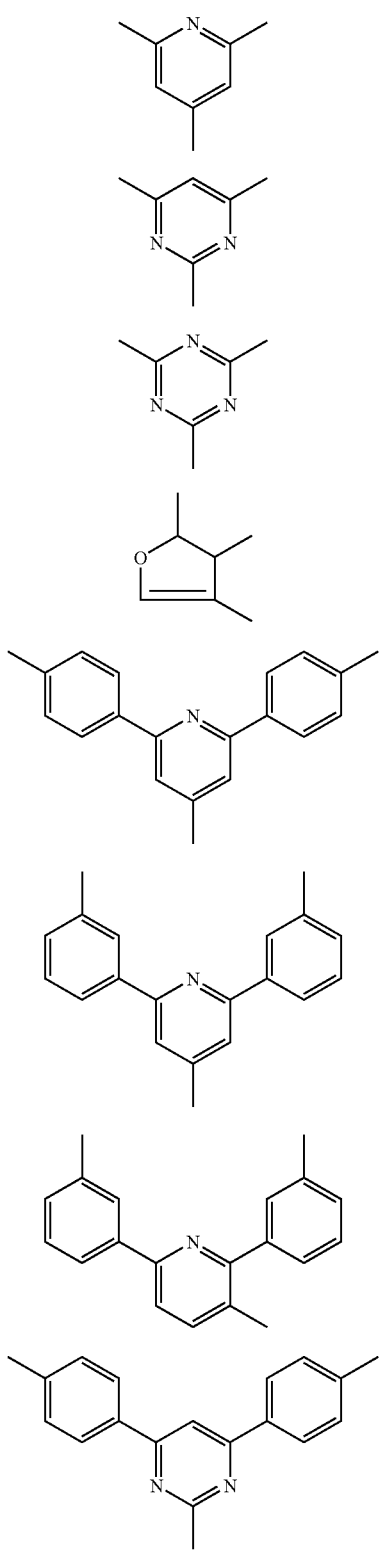

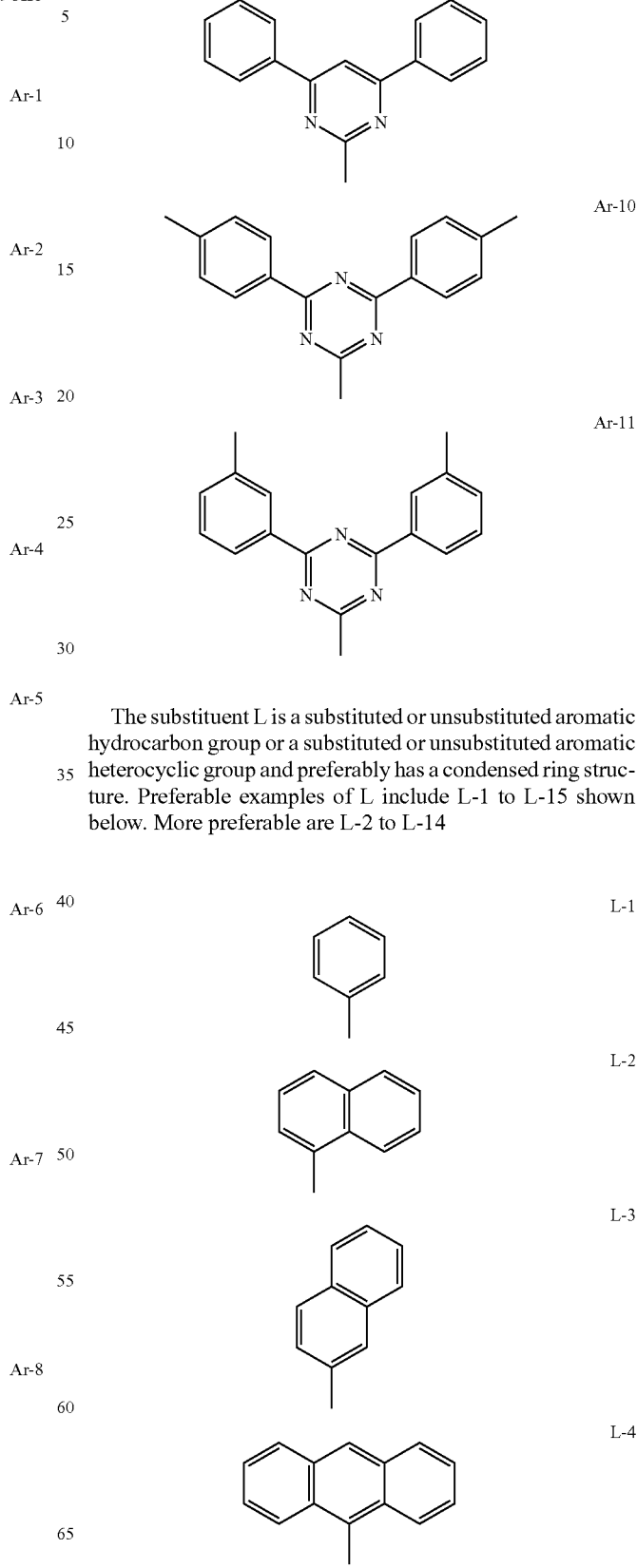

The substituent L is a substituted or unsubstituted aromatic hydrocarbon group or a substituted or unsubstituted aromatic heterocyclic group and preferably has a condensed ring structure. Preferable examples of L include L-1 to L-15 shown below. More preferable are L-2 to L-14

L-5 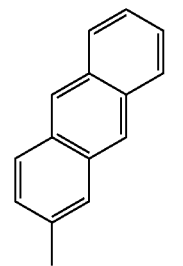
L-6 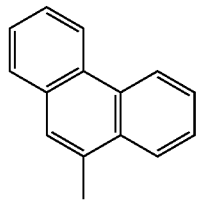
L-7 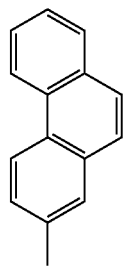
L-8 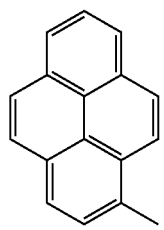
L-9 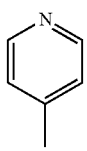
L-10 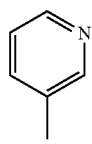
L-11 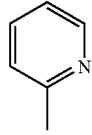
L-12 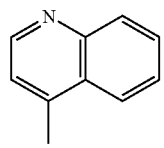
L-13 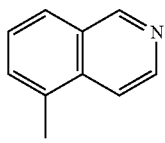
L-14 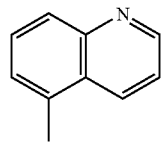
L-15 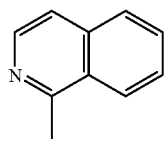
Preferable examples of the compounds represented by the aforementioned general formulas (I) to (IV) are shown below, but not limited thereto. Compounds 1 to 10 are represented by general formula (I) wherein m=1. Compounds 10 to 29 are represented by general formula (I) wherein m=2 and it is to be understood that they are listed as reference compounds.
1
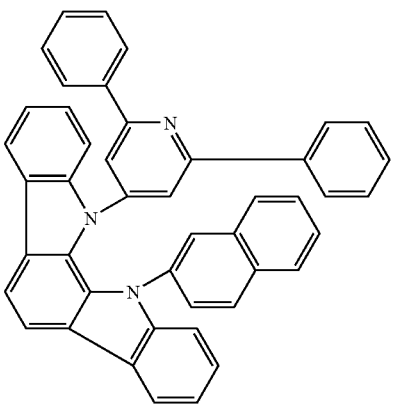
2
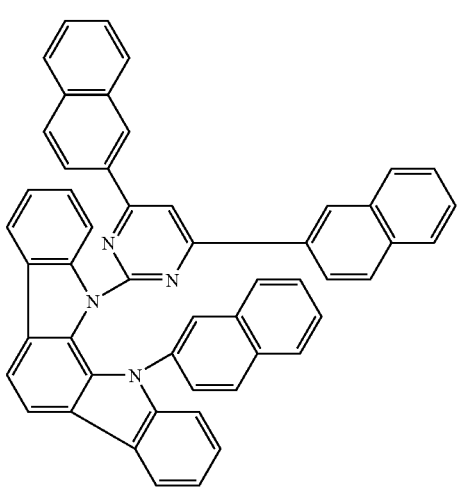

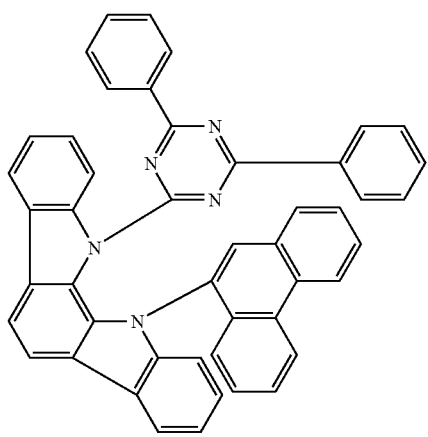
3
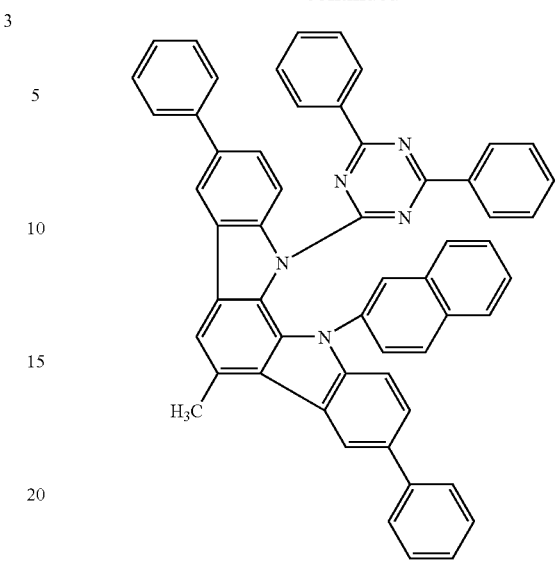
6
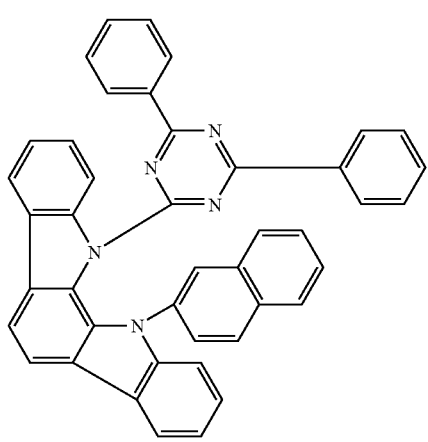
4
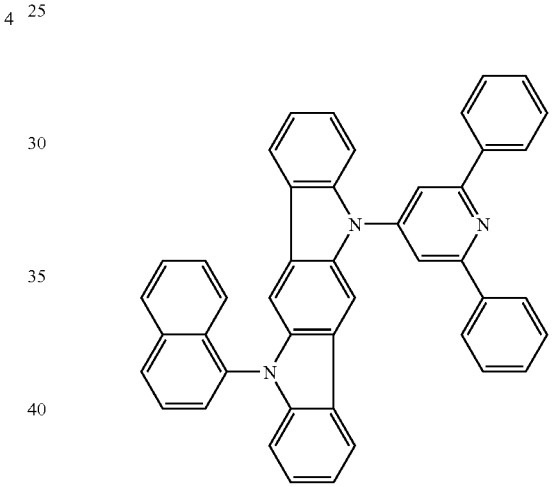
7
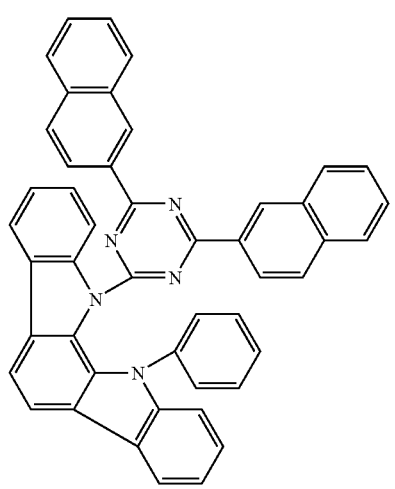
5
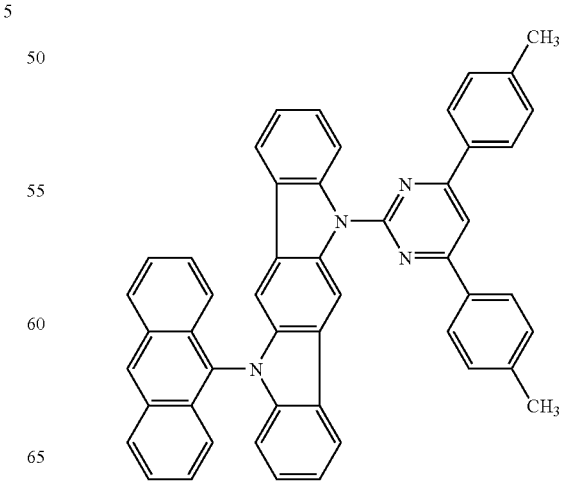
8

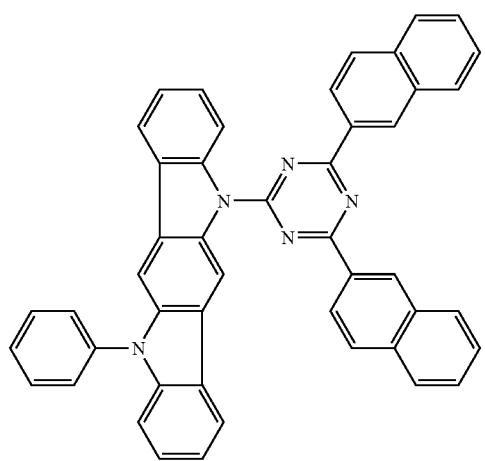
9
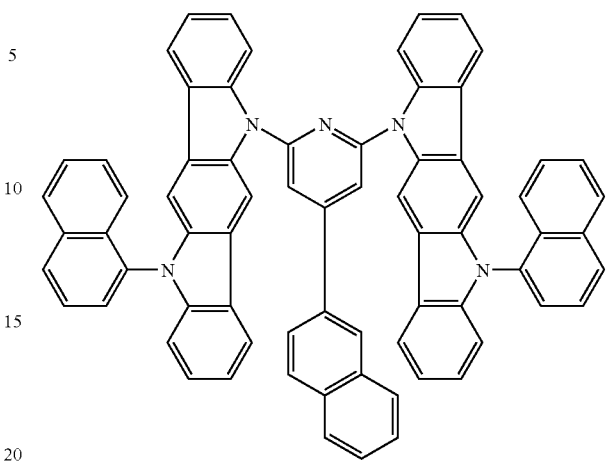
12
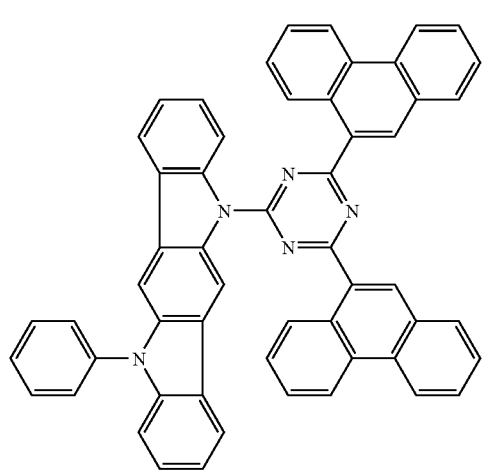
10
13
11
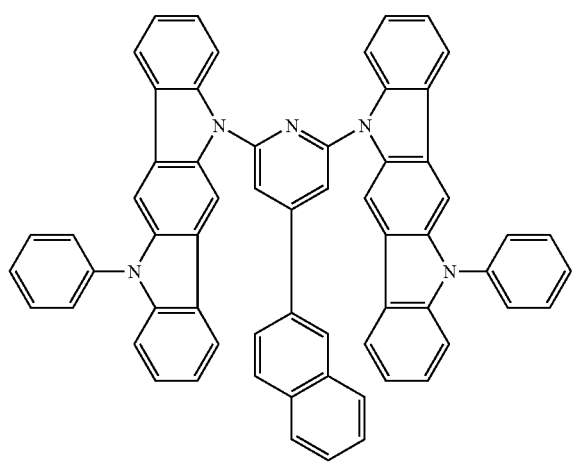
14

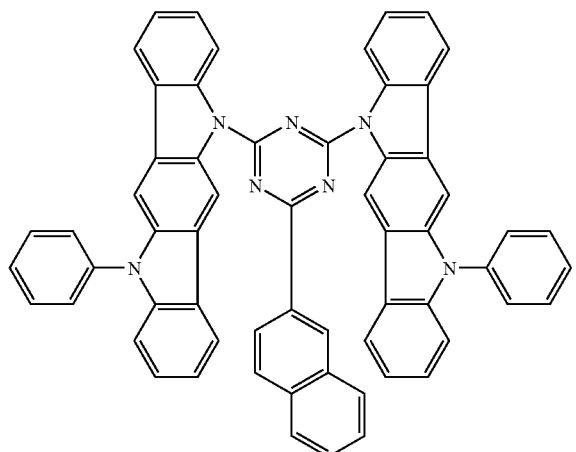
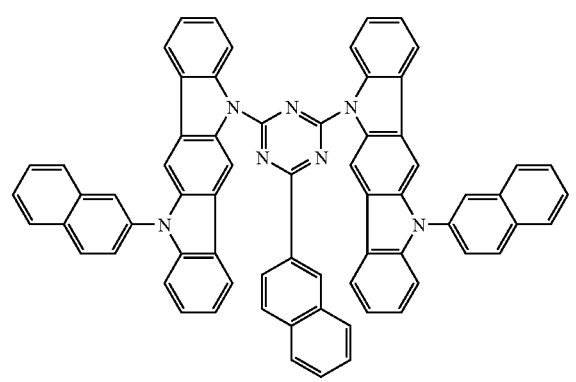
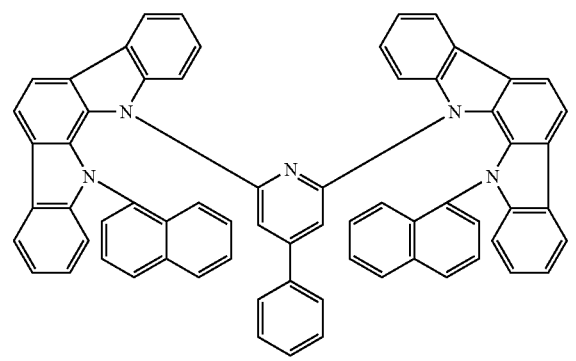
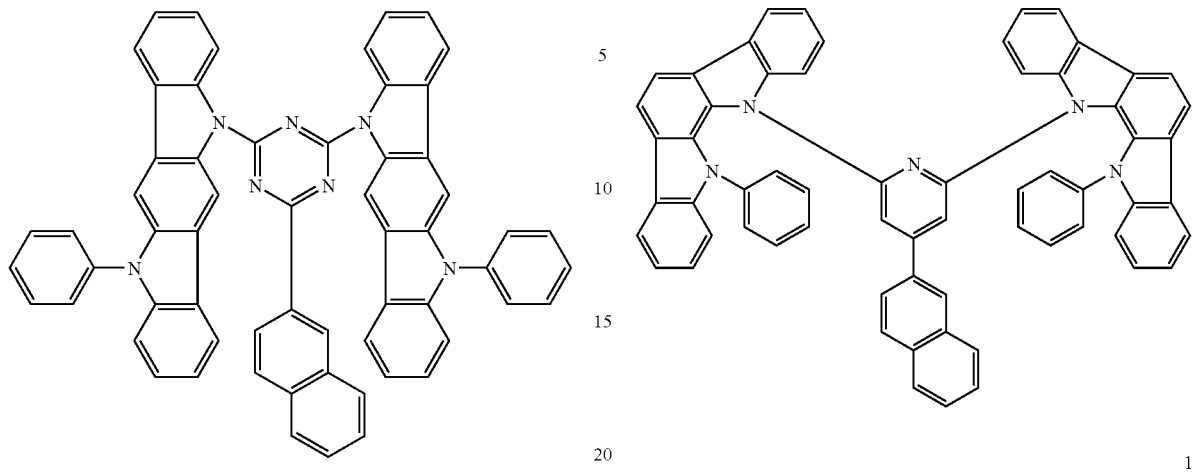
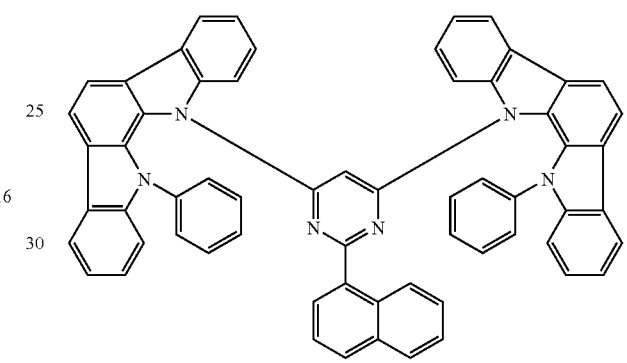
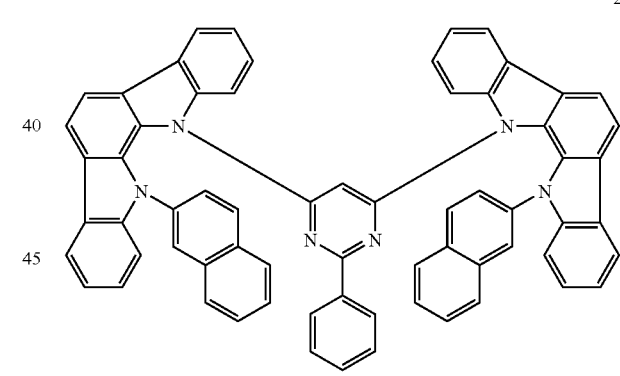
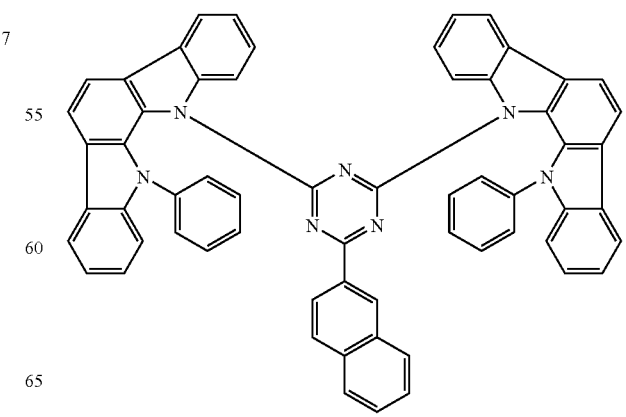

22
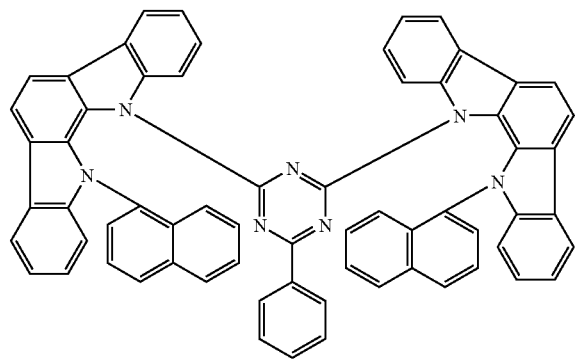
23
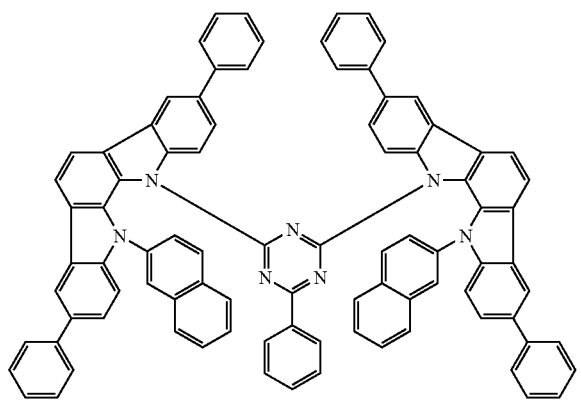
24
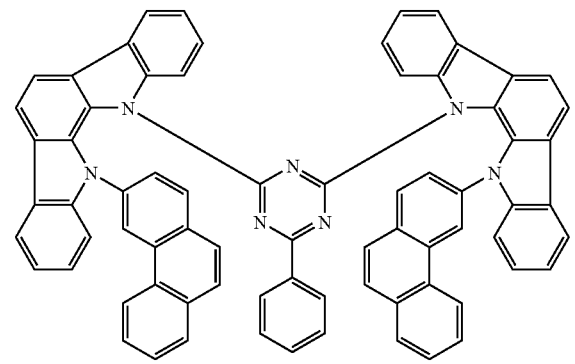
25
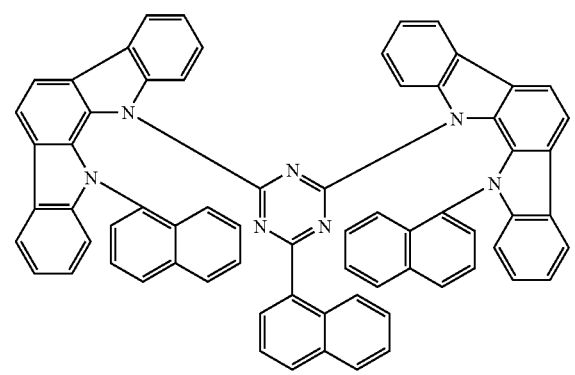
26
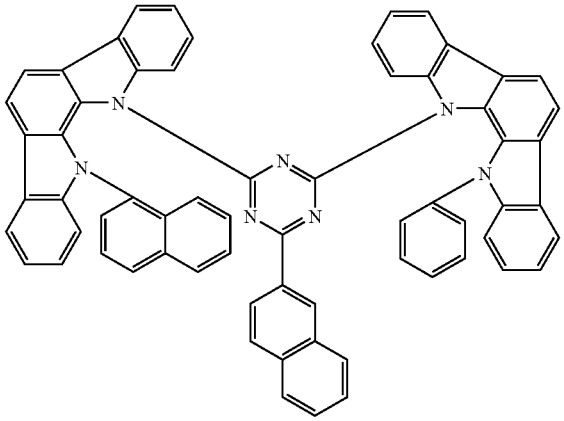
27
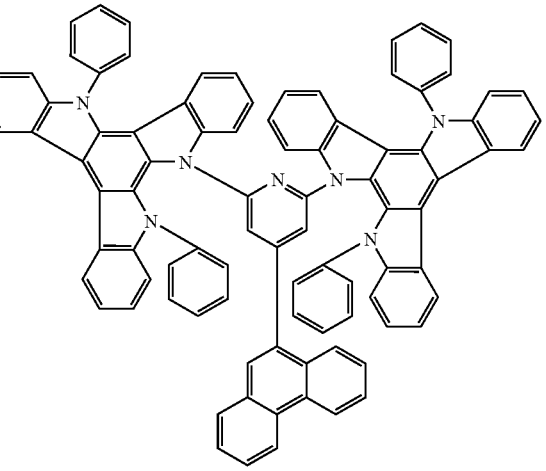
28

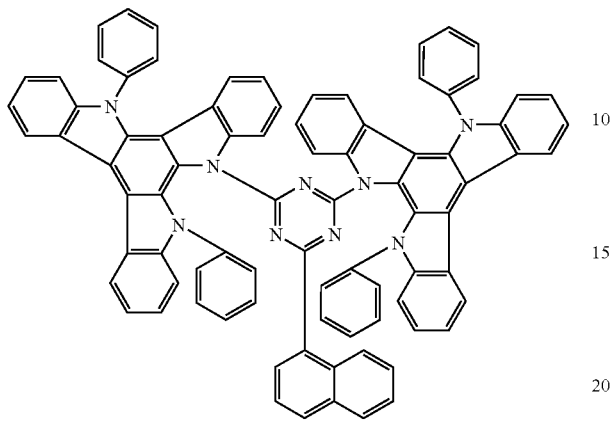

29

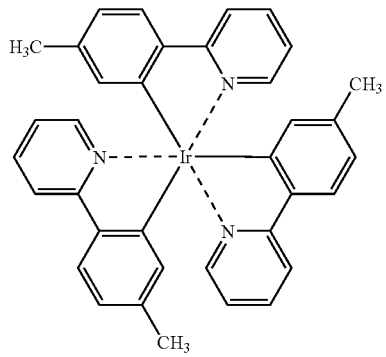

31

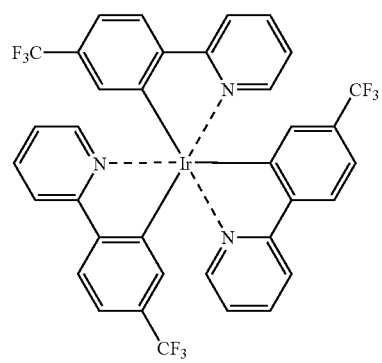

32

The organic EL device of this invention has at least one light-emitting layer disposed between an anode and a cathode piled one upon another on a substrate and said light-emitting layer comprises a phosphorescent dopant and the aforementioned compound for an organic EL device represented by any of general formulas (I) to (IV) as a host material. It is preferable that a hole injecting/transporting layer is disposed between the anode and the light-emitting layer and an electron injecting/transporting layer is disposed between the cathode and the light-emitting layer. It is also preferable that a hole-blocking layer is disposed between the light-emitting layer and the electron injecting/transporting layer.

Phosphorescent dopants to be used in the light-emitting layer are preferably organic metal complexes containing at least one metal selected from ruthenium, rhodium, palladium, silver, rhenium, osmium, iridium, platinum, and gold. Such organic metal complexes are known in the aforementioned patent documents and elsewhere and a suitable complex can be selected from them and used in this invention.

Preferable phosphorescent dopants include complexes having a noble metal element such as Ir in the center, typically Ir(ppy)3, complexes such as Ir(bt)2. acac3, and complexes such as PtOEt3. Examples of these complexes are shown below, but are not limited thereto.

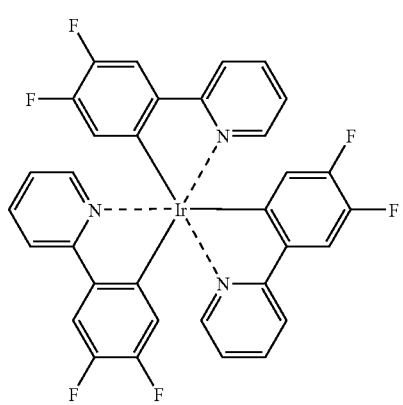

33

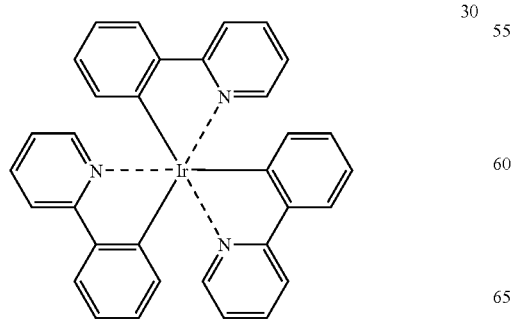

30

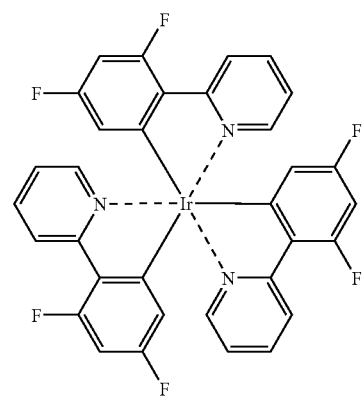

34

35
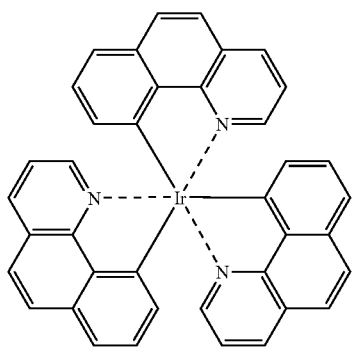
36
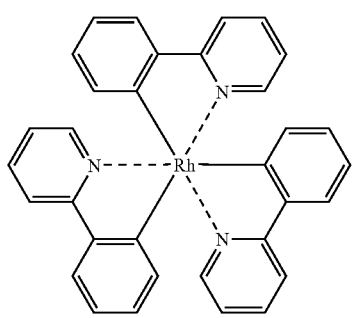
37
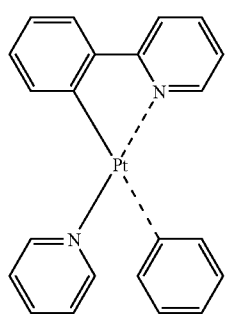
38
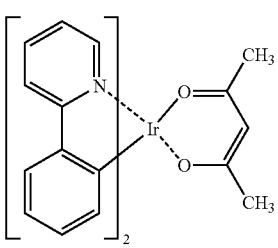
39
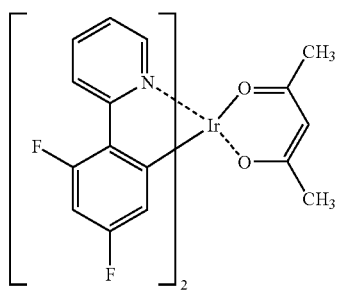
40
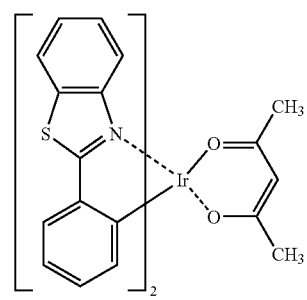
41
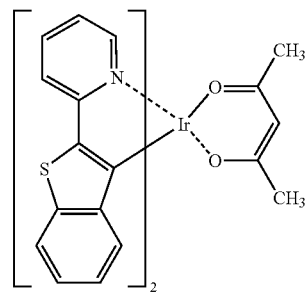
42
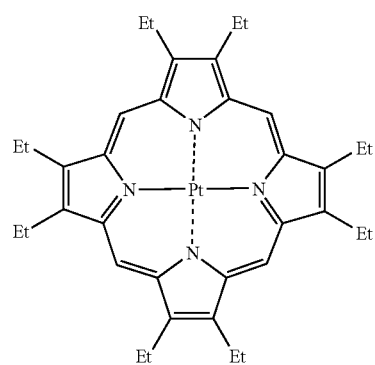
43
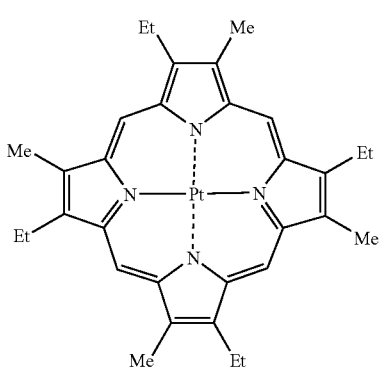

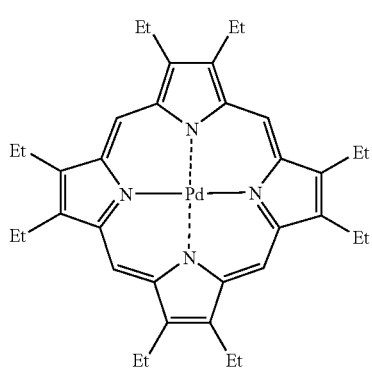

44

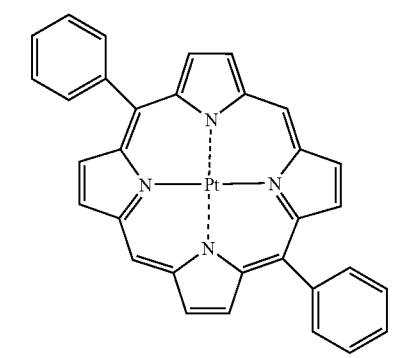

46

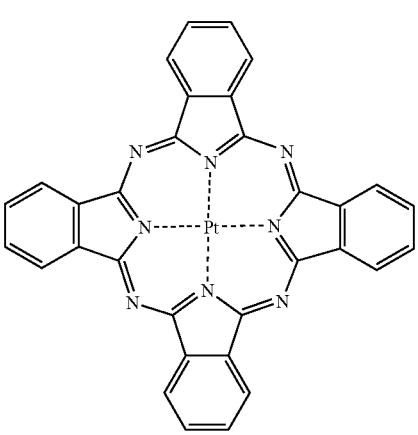

47

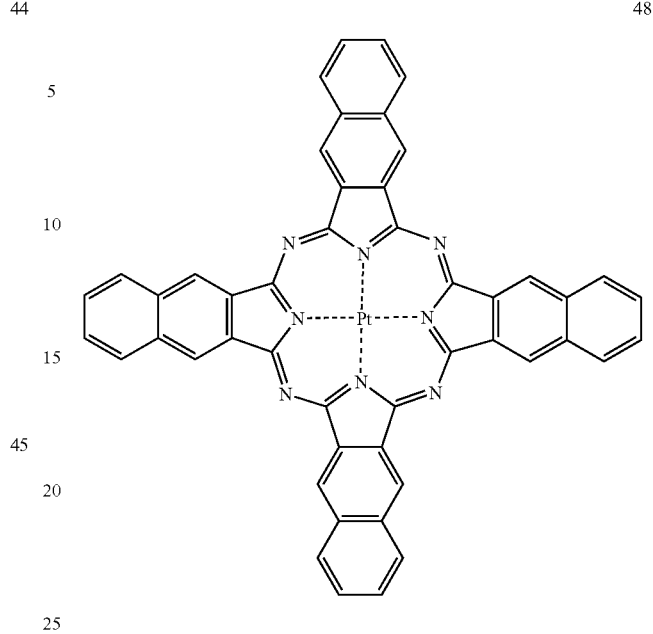

48

The content of the aforementioned phosphorescent dopant in the light-emitting layer is preferably in the range of 5 to 10 wt %.

Figure 1:
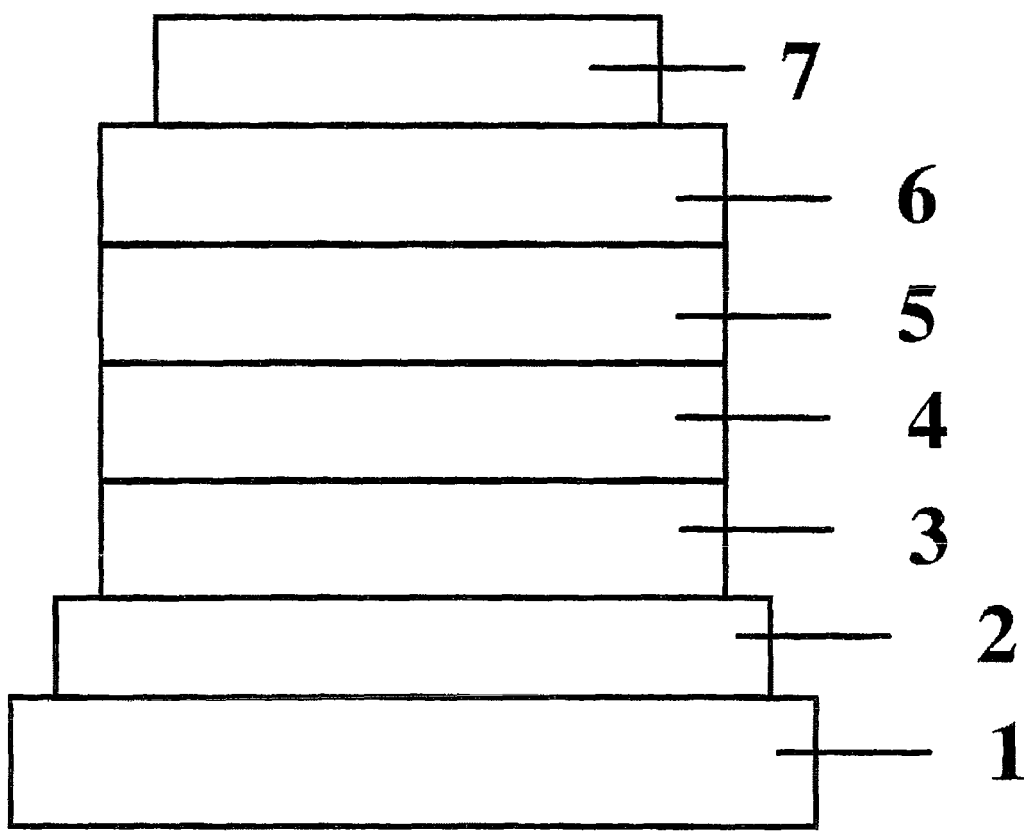
FIG. 1 schematically shows the cross section of an example of an organic EL device.

Explanation of symbols: 1 substrate; 2 anode; 3 hole-injecting layer; 4 hole-transporting layer; 5 light-emitting layer, 6 electron-transporting layer; 7 cathode.

PREFERRED EMBODIMENTS OF THE INVENTION

The structure of the organic EL device of this invention will be explained with reference to the drawing, but it will not be limited to the one shown in the drawing.

FIG. 1 schematically shows the structure of an example of an organic EL device generally used in this invention and 1 stands for a substrate, 2 for an anode, 3 for a hole-injecting layer, 4 for a hole-transporting layer, 5 for a light-emitting layer, 6 for an electron-transporting layer, and 7 for a cathode. The organic EL device of this invention comprises the substrate, the anode, the light-emitting layer, and the cathode as essential layers; in addition to the essential layers, the device preferably has a hole-injecting/transporting layer and an electron-injecting/transporting layer and, further, has a hole-blocking layer disposed between the light-emitting layer and the electron-injecting/transporting layer. The term hole-injecting/transporting layer means a hole-injecting layer and/or a hole-transporting layer and the term electron-injecting/transporting layer means an electron-injecting layer and/or an electron-transporting layer.

It is possible to fabricate a device with a structure that is the reverse of the one shown in FIG. 1 by piling the cathode 7, the electron-transporting layer 6, the light-emitting layer 5, the hole-transporting layer 4, and the anode 2 one upon another in this order on the substrate 1 and, as described earlier, it is possible to dispose the organic EL device of this invention between two substrates at least one of which is highly transparent. In this case of the reverse structure, a layer or layers may be added or omitted as needed.

The organic EL device of this invention is applicable to a single device, a device with its structure arranged in array, or a device in which the anode and the cathode are arranged in X-Y matrix. The organic EL device of this invention produces remarkable improvements in luminous efficiency and driving stability over the conventional devices utilizing emission of light from the excited singlet state by incorporating a compound of specific skeleton and a phosphorescent dopant in its light-emitting layer and the device can perform excellently when applied to full-color or multicolor panels.

EXAMPLES

This invention will be described in more detail below with reference to the examples; however, it will not be limited to these examples and it can be reduced to practice in various modes unless such practice exceeds the substance of this invention.

Example 1

Synthesis of Compound 21

In a 200-ml three-necked flask that had been deaerated and filled with nitrogen were placed 33.3 g (0.297 mole) of 1,2-cyclohexanedione and 86.0 g (0.595 mole) of phenylhydrazine hydrochloride, then 1,000 ml of ethanol was added, and the mixture was stirred. Then, 3.0 g (0.03 mole) of concentrated sulfuric acid was added dropwise to the flask over 5 minutes. The mixture was then heated to 65° C. and stirred at this temperature for 4 hours. The mixture was cooled to room temperature, the violet brown crystals formed were collected by filtration, washed twice by reslurrying with 500 ml of ethanol, and dried under reduced pressure to give 80.0 g (0.286 mole, 96.3% yield) of a violet brown powder.

Then, 720 g of acetic acid and 72.0 g of trifluoroacetic acid were added to 72.0 g (0.258 mole) of the aforementioned violet brown powder and stirred. The mixture was then heated to 100° C. and stirred at this temperature for 15 hours. The mixture was cooled to room temperature and the yellow crystals formed were collected by filtration. The crystals were rinsed with 200 ml of acetic acid, then rinsed with 200 ml of hexane, and dried under reduced pressure to give 30.0 g (0.117 mole, 45.3% yield) of a white powder A Next, in a 1,000-ml three-necked flask that had been deaerated and filled with nitrogen were placed 26.0 g (0.101 mole) of the white powder A obtained above, 122.7 g (0.601 mole) of iodobenzene, 54.7 g (0.287 mole) of copper iodide, 66.7 g (0.482 mole) of potassium carbonate, and 800 ml of quinoline and stirred. The mixture was then heated to 190° C. and stirred at this temperature for 72 hours. The mixture was cooled to room temperature, 500 ml of water and 500 ml of dichloromethane were added, the mixture was stirred, and the yellow crystals formed were collected by filtration. The filtrate was transferred to a 2,000-ml separatory funnel and separated into an organic layer and an aqueous layer. The organic layer was washed three times with 500 ml of water and then dehydrated over magnesium sulfate, the magnesium sulfate was filtered out, and the solvent was distilled off under reduced pressure. The residue was purified by column chromatography to give 13.7 g (0.04 mole, 40.8% yield) of a white powder B.

In a 500-ml three-necked flask that had been deaerated and filled with nitrogen were placed 2.16 g (0.0495 mole) of sodium hydride (55% dispersion) and 70 ml of dehydrated N,N'-dimethylformamide and the mixture was stirred under flow of nitrogen. To 13.7 g (0.04 mole) of the white powder B obtained above was added 70 ml of dehydrated N,N'-dimethylformamide and the resulting solution was added dropwise to the flask over 15 minutes. After the dropwise addition, the mixture was stirred continuously for 1 hour. Thereafter, a solution of 3.76 g (0.02 mole) of cyanuric chloride in 70 ml of dehydrated N,N'-dimethylformamide was added dropwise to the flask over 15 minutes. After the dropwise addition, the mixture was stirred continuously for 2 hours, 350 g of water was added, and the crystals separated were collected by filtration. The crystals were reslurried twice with 300 g of water, then reslurried with 300 g of methanol, dried under reduced pressure, and purified by column chromatography to give 10.9 g (0.014 mole, 70.0% yield) of a white powder C.

Then, 10.0 g (0.013 mole) of the white powder C obtained above, 2.8 g (0.016 mole) of 2-naphthylboronic acid, 1.5 g (0.0013 mole) of tetrakis(triphenylphosphine)palladium(0), 50 ml of ethanol, and 100 ml of toluene were placed in a 300-ml three-necked flask and stirred. To the flask was added a solution of 6.5 g of sodium carbonate in 50 ml of water and the mixture was heated to 85° C. and stirred at this temperature for 5 hours. The mixture was cooled to room temperature, 100 ml of water and 100 ml of toluene were added, the mixture was stirred, and the insoluble matters were separated by filtration. The filtrate was transferred to a 1,000-ml separatory funnel and separated into an organic layer and an aqueous layer. The organic layer was washed three times with 100 ml of water and then dehydrated over magnesium sulfate, the magnesium sulfate was filtered out, and the solvent was distilled off under reduced pressure. The residue was purified by column chromatography to give 34.7 g (0.04 mole, 40.8% yield) of Compound 21 illustrated in the specification as a yellow solid.

Compound 21 gave a fragment (M+1) with a mass of 868 in an analysis by EI-MS and showed a melting point of 398° C.

Example 2

Copper phthalocyanine (CuPC), α-NPD, and Alq3 were respectively used to form a hole-injecting layer, a hole-transporting layer, and an electron-transporting layer. They were deposited in thin films one upon another on a glass substrate having a 150 nm-thick ITO anode formed thereon by the vacuum deposition process at a degree of vacuum of $5.0 \times 10^{-4}$ Pa. First, CuPC was deposited on the ITO anode to a thickness of 25 nm at a rate of 3.0 Å/sec as a hole-injecting layer. Then, α-NPD was deposited on the hole-injecting layer to a thickness of 55 nm at a rate of 3.0 Å/sec as a hole-transporting layer.

Then, Compound 21 and (Btp)2Iracac (Compound 41 illustrated in the specification) were co-deposited on the hole-transporting layer from different evaporation sources to a thickness of 47.5 nm as a light-emitting layer. The concentration of (Btp)2Iracac at this time was 8.0%.

Then, Alq3 was deposited to a thickness of 30 nm at a rate of 3.0 Å/sec as an electron-transporting layer. Further, lithium fluoride (LiF) was deposited on the electron-transporting layer to a thickness of 1 nm at a rate of 0.1 Å/sec as an electron-injecting layer. Finally, aluminum (Al) as an electrode was deposited on the electron-injecting layer to a thickness of 200 nm at a rate of 10 Å/sec to complete the fabrication of an organic EL device.

Example 3

Synthesis of Compound 4

In a 200-ml three-necked flask that had been deaerated and filled with nitrogen were placed 10.0 g (0.036 mole) of the white powder A obtained in Example 1, 12.9 g (0.093 mole) of potassium carbonate, 5.7 g (0.090 mole) of copper powder, and 50.0 g of tetraglyme and stirred under flow of nitrogen. To the flask was added dropwise a solution of 9.87 g (0.047 mole) of 2-bromonaphthalene in 10.0 g of tetraglyme over 10 minutes. After the dropwise addition, the mixture was stirred at 195° C. for 1 hour. The mixture was then cooled to room temperature and the insoluble matters were separated by filtration. To the filtrate were added 30 g of methanol and 150 g of water and the mixture was stirred for 2 hours. Thereafter, a precipitate was collected by filtration, washed twice by reslurrying with 100 g of water, then washed once by reslurrying with 100 g of methanol, dried under reduced pressure, and purified by column chromatography to give 13.0 g (0.034 mole, 94.7% yield) of a white powder D.

Then, 12.5 g (0.068 mole) of cyanuric chloride and 50 g of dehydrated THF were placed in a 200-ml three-necked flask that had been deaerated and filled with nitrogen and cooled in an ice bath with stirring under flow of nitrogen. To this was added dropwise 105.6 g (0.186 mole) of a 32% THF solution of phenylmagnesium bromide over 2 hours. The temperature during the dropwise addition was kept at 15° C. or below. After the dropwise addition, the stirring was continued for 1.5 hours and then 80 g of toluene was added to the flask. The mixture was cooled in an ice bath and 76.5 g (0.254 mole) of 12% aqueous HCl was added dropwise over 15 minutes. The temperature during the dropwise addition was kept at 30° C. or below. The contents of the flask were transferred to a 500-ml separatory funnel and separated into an organic layer and an aqueous layer. The organic layer was washed three times with 100 ml of water and then dehydrated over magnesium sulfate, the magnesium sulfate was filtered out, and the solvent was distilled off under reduced pressure to give 21.1 g of a crude product. Thereafter, 110 g of methanol was added, the mixture was stirred for 1 hour, and a precipitate was collected by filtration and dried under reduced pressure to give 14.5 g (6.5 millimoles, 50.2% yield) of a white powder E.

Then, 1.31 g (0.033 mole) of sodium hydride (60.8% dispersion) and 10 ml of dehydrated N,N'-dimethylformamide were placed in a 200-ml three-necked flask that had been deaerated and filled with nitrogen and stirred under flow of nitrogen. To this was added dropwise a solution of 10.0 g (0.026 mole) of the white powder D obtained above in 30 ml of dehydrated N,N'-dimethylformamide over 20 minutes. After the dropwise addition, the stirring was continued for 1 hour. Then, to this mixture was added dropwise a solution of 6.75 g (0.025 mole) of the white powder E obtained above in 10 ml of dehydrated N,N'-dimethylformamide over 20 minutes. After the dropwise addition, the stirring was continued for 17 hours. Thereafter, 3.2 g of water and 40.0 g of methanol were added in succession and the crystals separated were collected by filtration, washed by reslurrying with 50 g of methanol, and dried under reduced pressure to give 12.8 g (0.021 mole, 80.0% yield) of Compound 4 illustrated in the specification as light yellow crystals.

Compound 4 gave a fragment $[M+H]^+$ at m/z=614 in an analysis by APCI-MS and showed a melting point of 317° C.

Example 4

An organic EL device was fabricated as in Example 2 with the exception of using Compound 4 in place of Compound 21 as a host material of the light-emitting layer.

Example 5

Synthesis of Compound 5

In a 500-ml three-necked flask that had been deaerated and filled with nitrogen were placed 3.65 g (0.150 mole) of magnesium, 10.0 g of dehydrated THF, and 0.01 g of iodine were placed and stirred under flow of nitrogen. The mixture was heated to 60° C. and a solution of 32.1 g (0.155 mole) of 2-bromonaphthalene in 100.0 ml of dehydrated THF was added dropwise over 1 hour. Then, the mixture was heated under reflux with stirring for 2 hours. The mixture was cooled to room temperature, then cooled further to 3° C. in an ice bath. To this was added dropwise a solution of 9.21 g (0.050 mole) of cyanuric chloride in 50.0 ml of dehydrated THF over 30 minutes while keeping the reaction mixture at 10° C. or below in an ice bath. After the dropwise addition, the stirring was continued at room temperature for 5 hours. Then, the flask was immersed in an ice bath and 50.0 g of 10% aqueous hydrochloric acid was added dropwise over 30 minutes while keeping the temperature at 15° C. or below. The ice bath was removed and 150.0 ml of toluene was added to the mixture. The mixture was transferred to a 500-ml separatory funnel and separated into an organic layer and an aqueous layer. The organic layer was washed three times with 50 ml of water and then dehydrated over magnesium sulfate, the magnesium sulfate was filtered out, and the solvent was distilled off under reduced pressure to give 33.6 g of a concentrate. The concentrate was dissolved in 75.0 g of THF and to the resulting solution was added slowly 200.0 g of methanol with stirring. The crystals separated were collected by filtration and recrystallized from hexane to give 7.6 g (0.021 mole, 41.3% yield) of a white powder F.

Then, 0.98 g (0.025 mole) of sodium hydride (60.8% dispersion) and 10 ml of dehydrated N,N'-dimethylformamide were placed in a 200-ml three-necked flask that had been deaerated and filled with nitrogen and stirred under flow of nitrogen. To this was added dropwise a solution of 6.45 g (0.019 mole) of the white powder B obtained in Example 1 in 20 ml of dehydrated N,N'-dimethylformamide over 20 minutes. After the dropwise addition, the stirring was continued for 1 hour. The mixture was cooled in an ice bath and a solution of 7.0 g (0.019 mole) of the white powder F in 10 ml of dehydrated N,N'-dimethylformamide was added dropwise over 10 minutes while keeping the temperature inside the flask at 5° C. or below. After the dropwise addition, the mixture was further stirred at room temperature for 7 hours. Then, 4.0 g of water and 100.0 g of methanol were added to the mixture and the crystals separated were collected by filtration. The crystals were washed by reslurrying with 50 g of methanol and dried under reduced pressure to give 8.0 g (0.012 mole, 62.1% yield) of Compound 5 illustrated in the specification as yellow crystals.

Compound 5 gave a fragment $[M+H]^+$ at m/z=664 in an analysis by APCI-MS and showed a melting point of 355° C.

Example 6

An organic EL device was fabricated as in Example 2 with the exception of using Compound 5 in place of Compound 21 as a host material of the light-emitting layer.

Example 7

Comparative Example

An organic EL device was fabricated as in Example 2 with the exception of using BAlq in place of Compound 21 as a host material of the light-emitting layer.

The peak wavelength of emitted light, maximum luminous efficiency, and luminance half life (initial luminance, 2,000 cd/m$^2$) of the organic EL devices fabricated in the examples are shown in Table 1.

TABLE 1

|  | Peak wavelength of emitted light (nm) | Maximum luminous efficiency (cd/A) | Luminance half life (hr) |
| --- | --- | --- | --- |
| Example 2 | 620 | 9.2 | 3000 |
| Example 4 | 620 | 9.0 | 4500 |
| Example 6 | 620 | 8.9 | 18000 |
| Example 7 | 620 | 8.8 | 1500 |

INDUSTRIAL APPLICABILITY

The organic EL device of this invention can emit light of high luminance at high efficiency with application of low voltage. In consequence, the organic EL device of this invention is applicable to flat panel displays (for example, office computers and wall-hanging television sets), vehicle display devices, cellular phone displays, light sources utilizing the characteristics of planar light emitters (for example, light sources of copiers and backlight sources of liquid crystal displays and instruments), signboards, and beacon lights and has a high technical value.

The invention claimed is:

1. A compound for an organic electroluminescent device represented by the following general formula (I):

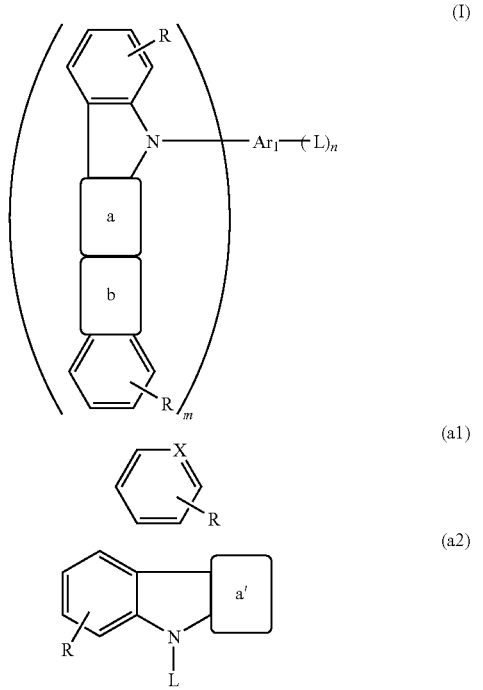

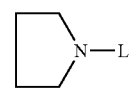

wherein, ring a is an aromatic or heterocyclic ring condensed with two adjacent rings and represented by formula (a1) or (a2), ring a' is an aromatic or heterocyclic ring condensed with three adjacent rings and represented by formula (a1), X is CH or N, and ring b is a heterocyclic ring condensed with two adjacent rings and represented by formula (b1);

Ar$_1$ is an aromatic heterocyclic group with a valence of m+n,

L is independently a substituted or unsubstituted aromatic hydrocarbon group or a substituted or unsubstituted aromatic heterocyclic group and at least one has a condensed ring structure;

R is independently hydrogen, alkyl group, aralkyl group, alkenyl group, alkynyl group, cyano group, dialkylamino group, diarylamino group, diaralkylamino group, amino group, nitro group, acyl group, alkoxycarbonyl group, carboxyl group, alkoxyl group, alkylsulfonyl group, haloalkyl group, hydroxyl group, amide group, a substituted or unsubstituted aromatic hydrocarbon group, or a substituted or unsubstituted aromatic heterocyclic group;

m is 1 and n is 1 or 2.

2. The compound for an organic electroluminescent device as claimed in claim 1, wherein the compound is represented by the following general formula (II):

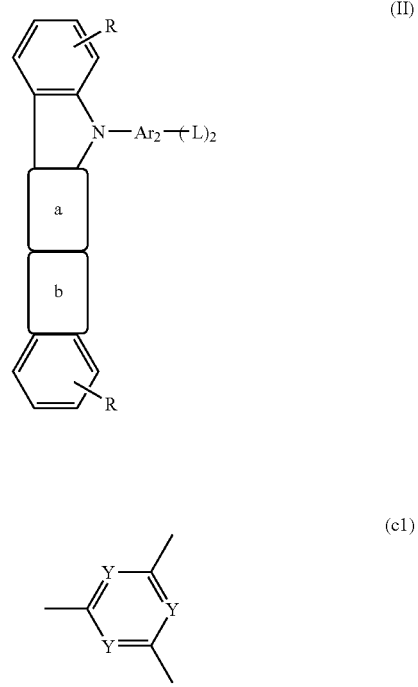

wherein, ring a, ring b, L, and R respectively have the same meaning as ring a, ring b, L, and R in general formula (I), Ar$_2$ is a trivalent group represented by formula (c1), and Y is independently CH or N and at least one is N.

3. The compound for an organic electroluminescent device as described in claim 2 wherein the compound is represented by the following general formula (III) or (IV),

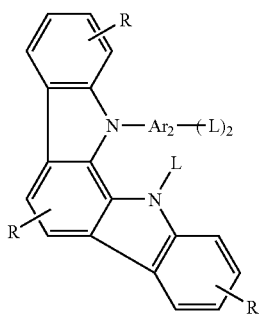

(III)

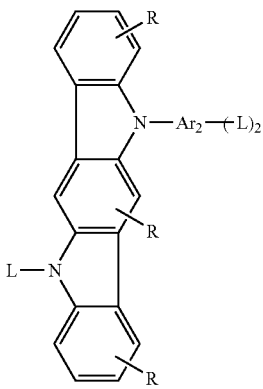

(IV)

In general formulas (III) and (IV),

L, R, and Ar$_2$ respectively have the same meaning as L, R, and Ar$_2$ in general formula (II).

4. An organic electroluminescent device comprising a light-emitting layer disposed between an anode and a cathode piled one upon another on a substrate wherein the light-emitting layer contains a phosphorescent dopant and the compound for an organic electroluminescent device described in any one of claims 1 to 3 as a host material.

5. The organic electroluminescent device as described in claim 4 wherein a hole injecting/transporting layer is disposed between the anode and the light-emitting layer and an electron injecting/transporting layer is disposed between the cathode and the light-emitting layer.

6. The organic electroluminescent device as described in claim 5 wherein a hole-blocking layer is disposed between the light-emitting layer and the electron injecting/transporting layer.

* * * * *